United States Patent [19]

Clark

[11] Patent Number: 5,750,043
[45] Date of Patent: May 12, 1998

[54] FLUOROCHEMICAL FOAM STABILIZERS AND FILM FORMERS

[75] Inventor: Kirtland P. Clark, West Greenwich, R.I.

[73] Assignee: Dynax Corporation, Elmsford, N.Y.

[21] Appl. No.: 296,003

[22] Filed: Aug. 25, 1994

(Under 37 CFR 1.47)

[51] Int. Cl.$^6$ ............................................. A62D 1/00
[52] U.S. Cl. .................... 252/2; 252/3; 528/332; 562/556
[58] Field of Search ................ 252/2, 3; 528/332; 562/556

[56] References Cited

U.S. PATENT DOCUMENTS

| | | | |
|---|---|---|---|
| 2,977,295 | 3/1961 | Jen | 117/72 |
| 3,769,307 | 10/1973 | Moreau et al. | 260/104.5 |
| 3,957,657 | 5/1976 | Chiesa, Jr. | 252/3 |
| 4,060,132 | 11/1977 | Chiesa, Jr. | 169/47 |
| 4,060,489 | 11/1977 | Chiesa, Jr. | 252/3 |
| 4,149,599 | 4/1979 | Chiesa, Jr. | 169/47 |
| 4,303,534 | 12/1981 | Hisamoto et al. | 252/3 |
| 4,306,979 | 12/1981 | Tsuji | 252/3 |
| 4,387,032 | 6/1983 | Chiesa, Jr. | 252/3 |
| 4,420,434 | 12/1983 | Falk | 260/501.12 |
| 4,424,133 | 1/1984 | Mulligan | 252/8.05 |
| 4,460,480 | 7/1984 | Kleiner et al. | 252/8.05 |
| 4,472,286 | 9/1984 | Falk | 252/3 |
| 4,563,287 | 1/1986 | Hisamoto | 252/2 |
| 4,644,267 | 2/1987 | Chiesa, Jr. et al. | 252/8.05 |
| 4,859,349 | 8/1989 | Clark et al. | 252/3 |
| 4,999,119 | 3/1991 | Norman et al. | 252/3 |
| 5,085,786 | 2/1992 | Alm et al. | 252/8.05 |
| 5,218,021 | 6/1993 | Clark et al. | 254/56 |

*Primary Examiner*—Richard L. Raymond

[57] ABSTRACT

This invention relates to water soluble fluorochemical foam stabilizers and film formers derived from polyamines, perfluoroalkyl group containing esters or acid halides and hydrophilic and hydrophobic group containing compounds which react with primary, secondary and tertiary amino groups. The novel foam stabilizers and film formers are useful as additives for aqueous film forming foam fire fighting agents improving the foam stability against polar solvents and enhancing the fire fighting performance.

15 Claims, No Drawings

FLUOROCHEMICAL FOAM STABILIZERS AND FILM FORMERS

BACKGROUND OF THE INVENTION

The instant invention related to novel water soluble fluorochemical foam stabilizers and film formers useful as additives to aqueous film forming foam agents improving the stability of foams of such agents when in contact with polar solvents and fuels, improving the fire performance of such foams and allowing the formulation of aqueous film forming agents having Newtonian properties.

Fire fighting foam concentrates which produce aqueous film forming foams are known a) as AFFF agents (for Aqueous Film Forming Foam) if they have the capability of extinguishing non-polar solvent or fuel fires and b) as AR-AFFF agents (for Alcohol Resistant AFFF agent) if they have the capability of extinguishing polar as well as non-polar solvent or fuel fires. Aqueous film forming foams are the most efficient fire fighting agents because the act in the following two ways as outlined in U.S. Pat. No. 4,472,286:

a) As aqueous foams they are used as primary fire extinguishing agents and b) As aqueous film formers they act as vapor suppressors, augmenting the fire-extinguishing efficiency of the foam and prevent reignition of fuel of solvent vapors.

It is the second property which makes AFFF and AR-AFFF agents far superior to other known fire fighting agents. With AFFF and AR-AFFF agents, the vapor sealing action on non-polar solvents and fuels is achieved by the spreading of the aqueous agent solution draining from the foam onto the non-polar solvent and fuel surfaces, while with AR-AFFF agents, the vapor sealing action on polar solvents and fuels is achieved by the precipitation of a polymer film from a polymer solution draining from the foam onto the polar solvent surface and the spreading of the aqueous film forming solution, also draining from the AR-AFFF foam, over the surface of the precipitated polymer film.

The criterion necessary to attain a spontaneous spreading of two immiscible liquids has been taught by Harkins et al, *Journal of American Chemistry*, 44, 2665 (1922).

The measure of the tendency for spontaneous spreading of an aqueous solution over the surface of non-polar solvents such as hydrocarbons is defined by the spreading coefficient (SC) and can be expressed as follows:

$$SC_{a/b} = Y_b - Y_a - Y_f$$

where $SC_{a/b}$=Spreading coefficient $Y_b$=Surface tension of the lower hydrocarbon fuel phase.

$Y_a$=Surface tension of the upper aqueous phase.

$Y_f$=Interfacial tension between the aqueous upper phase and the lower hydrocarbon phase.

If the SC is positive, an aqueous solution should spread and film formation on top of the hydrocarbon surface should occur. The more positive the SC, the greater the spreading tendency will be.

For example, if a hydrocarbon fuel has a surface tension of 20 dynes/cm and aqueous solution has a surface tension of 16 dynes/cm and the interfacial tension between the two immiscible liquids is 1.0 dyne/cm, then the spreading coefficient (SC) will be +3(SC=20–16–1=+3) and therefore film formation will occur.

Today's AFFF and AR-AFFF agents contain one or more fluorochemical surfactants providing the desired low surface tension of 15 to 18 dynes/cm, one or more hydrocarbon surfactants providing the desired interfacial tension of 1 to 5 dynes/cm as well as the desired foam properties such as foam expansion, foam fluidity and foam drainage, fluorochemical synergists to improve the efficiency of fluorochemical surfactants, foam stabilizers, solvents, electrolytes, pH buffers, corrosion inhibitors and the like. In addition to the above components in AFFF agents, AR-AFFF agents contain one or more water-soluble polymers which precipitate on contact with a polar solvent or fuel, providing a protecting polymer film at the interface between fuel and the aqueous film forming foam. Many U.S. patents describe the composition of AFFF agents as summarized in U.S. Pat. No 4,999,119. Additional AFFF agent compositions are also described in U.S. Pat. Nos. 4,420,434; 4,472,286; 5,085,786 and 5,218,021.

Compositions of AR-AFFF agents using thixotropic polysaccharide gums as water-soluble polymers which precipitate on contact with polar solvents or fuels and which were found to be the most efficient polymeric film formers are described in U.S. Pat. Nos. 3,957,657; 4,060,489; 4,149,599; 4,306,979; 4,387,032; 4,644,267; 4,060,132 and 4,999,119.

Unlike regular AFFF agents foams which collapse within seconds upon contact with polar solvents and fuels, AR-AFFF agent foams based on thixotropic polysaccharides have foam stabilities ranging from about a minute up to 10 minutes before collapsing. While the development of AR-AFFF agents based on thixotropic gums has been a significant progress since AR-AFFF agents can be used to fight both polar and non-polar solvent fires, they have nevertheless shown to have a number of deficiencies.

In order for AR-AFFF agents to be efficient in fighting polar solvent fires, it was found that AR-AFFF agents for 6 and 3% proportioning with fresh or sea water require from 1 to 1.5% of thixotropic polysaccharide to be efficient film formers providing the required foam stability and therefore fire fighting efficiency.

At these polysaccharide levels, AR-AFFF agents are thixotropic gel like materials with viscosities as high as 5000 centipoise which only upon application of shear will turn into fluid and readily flowable agents which can be proportioned with water. In addition, polysaccharides as natural products are readily biodegradable and oxidizable and upon aging, AR-AFFF agents were found to form solid blocks of gum on the surface of AR-AFFF agents. Furthermore, polysaccharide gums are not soluble in solvents used as antifreeze, and it is therefore not possible to produce freeze-protected AR-AFFF agents protected to temperature much below zero °C.

In U.S. Pat. No. 4,424,133 AR-AFFF agents are described using polysaccharide gums in combination with protein hydrolysates and U.S. Pat. No. 4,859,349 discloses the use of complexes of anionic polysaccharides and cationic fluorochemical surfactants.

U.S. Pat. No. 4,303,534 describes foam fire fighting compositions comprising fluorochemical and hydrocarbon surfactants, hydrolized protein and a water soluble high molecular weight compound having several repeating units containing a fluoroalkyl group and a water solubilizable group having a fluorine content of not less than 10% and a molecular weight of not less than 5,000 useful for fighting polar solvent fires.

U.S. Pat. No. 4,563,287 describes a non-foaming cooking oil fire extinguishing composition comprising a water soluble high molecular weight compound as described in U.S. Pat. No. 4,303,534 having a fluorine content of not less than 15%.

It has now been surprisingly found that novel water soluble oligomeric and polymeric additives derived from oligomeric and polymeric amines, esters or halides of perfluoroalkyl group containing acids and optionally and preferably hydrophilic group containing compounds and optionally hydrophobic group containing compounds capable to react with primary, secondary or tertiary amino groups are useful additives to aqueous film forming agents of both the AFFF and AR-AFFF type acting as foam stabilizers and film formers, improving the performance of such agents. Depending on the structure and molecular weight of the instant additives, they also act as foaming agents.

Fluoroamide-amino polymers derived from polyethyleneimines and perfluoroalkyl esters are described in U.S. Pat. No. 3,769,307 as oil repellent finishes for cellulosic textiles. Such fluoroamide-amino polymers were found to be useful as foam stabilizers and film formers; however, they were found to be considerably less effective than foam stabilizers and film formers derived from polyamines, where a part of the primary and secondary amines were reacted with $R_f$-group containing esters or acid halides and essentially all of the remaining primary and secondary amino groups were reacted with hydrophilic group and optionally with hydrophobic, non-fluorochemical group containing reactants.

More specifically, the instant additives, referred to as Foam Stabilizers or FS-additives, act similarly as polysaccharides act in AR-AFFF agents. The FS-additives are, like polysaccharides soluble in water, but insoluble in polar solvents so they will precipitate from an aqueous film forming foam containing the instant FS-additives and form a liquid or solid film at the polar solvent/foam interface and prevent the further collapse and destruction of the aqueous film forming foam. Because the instant FS-additives contain perfluoroalkyl groups, they also improve the burnback resistance of aqueous film forming foams the same way as water soluble $R_f$-group containing oligomers and polymers act which are derived from perfluoroalkyl group containing mercaptans and hydrophilic monomers such as acryl amine, as described in U.S. Pat. No. 4,460,480.

These performance properties make the instant FS-additives useful in several ways as additives to aqueous film forming foam agents:

As additives to polysaccharide based AR-AFFF agents, they will improve the polar solvent foam stability without increasing the viscosity and without affecting or only marginally affecting other agent properties.

The FS-additives can also be used as partial replacements of polysaccharide in classical AR-AFFF agents, yielding lower viscosity AR-AFFF agents, still having some of the beneficial effects of the polysaccharide additive, such as long foam drainage times, and much better polar solvent foam stability than classical AR-AFFF agents.

Furthermore, and most importantly, the instant FS-additives can be used as additives to AFFF agents, yielding Newtonian AR-AFFF agents having as low a viscosity as regular AFFF agents and non-thixotropic properties. Newtonian AR-AFFF agents yield foams which are more fluid than non-Newtonian AR-AFFF agents containing polysaccharides, show faster control and extinguishment times and longer foam lives. If used on non-polar solvents, Newtonian AR-AFFF agents have increased burnback resistance when compared with the corresponding AFFF agent not containing the instant FS-additive.

Finally, the instant FS-additives can be used as additives to protein foams and fluoroprotein foams yielding improved burnback resistance and improved foam stability against polar solvents.

DETAILED DISCLOSURE

The present invention pertains to novel water soluble fluorochemical foam stabilizers and film formers useful as additives to aqueous film forming foam agents, improving the foam stability on polar solvents and therefore improving the extinguishment and the burnback resistance of these agents.

The present invention, furthermore, pertains to so-called alcohol resistant AFFF agents (AR-AFFF agents) having a reduced or no polysaccharide content and, therefore, significantly reduced viscosity, making it possible to produce AR-AFFF agents which are Newtonian or non-thixotropic and which can be produced in higher concentrations than today's AR-AFFF agents for 3% proportioning.

The novel additives, referred to as previously indicated as Foam Stabilizers or FS-additives, are water soluble oligomers and polymers derived from polyamines containing one or more Segment A, optionally and preferably one or more Segment B and optionally one or more Segment C.

Segment A are segments of formula Ia and Ib containing an oleophobic and hydrophobic perfluoroalkyl group.

(Ia)

(Ib)

wherein $R_f$ is independently a straight or branched perfluoroalkyl group or 4 to 20 carbon atoms or said perfluoroalkyl substituted by perfluoroalkoxy of 2 to 6 carbon atoms.

E is either zero or independently a divalent linking group and can be a straight or a branched alkylene group of 1 to 16 carbon atoms or said alkylene group interrupted by one to three groups selected from the group consisting of $-NHR_1-$, $-O-$, $-S-$, $-SO_2-$, $-COO-$, $-OOC-$, $-CONR_1-$, $-NR_1CO-$, $-SO_2NR_1-$, $-NR_1SO_2-$ or terminated at the $R_f$-end with $-CONR_1-$ OR $-SO_2NR_1-$, where $R_f$ is attached to the carbon or sulfur atom and wherein $R_1$ is independently hydrogen or alkyl of 1 to 6 carbon atoms.

W is $-CO-$ or $-SO_2-$;

m is 2 to 10 and p and q are 0 to 500 and p+q are equal or larger than 1.

Preferably, $R_f$ is a straight perfluoroalkyl group with 6 to 12 carbon atoms, E is zero or alkylene with 1 to 6 carbon atoms if W is $-CO-$ or $-SO_2-$ and $-CH_2CH_2SCH_2CH_2-$, $-CH_2CH_2SCH_2-$ or $-CH_2CH_2OCH_2CH_2-$, if W is $-CO-$; m is 2 and p and q are 1 to 100.

Segment B are segments of formula IIa, IIb and IIc containing a hydrophilic group

(IIa)

(IIb)

-continued

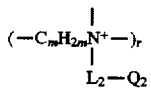

wherein $L_1$ is a divalent linking group and can be a straight or branched saturated or unsaturated hydrocarbon group of 1 to 16 carbon atoms or said hydrocarbon group interrupted by one to three groups selected from —$NHR_1$—, —O—, —S—, —$CONR_1$—, —$NR_1CO$—, —$SO_2NR_1$—, —$NR_1SO_2$ or terminated with —CO— or —$SO_2$— where the linking group $L_1$ is attached to the nitrogen in formula IIa or IIb;

$L_2$ is alkylene with 1 to 4 carbons;

$Q_1$ is a hydrophilic group and can be —COOH, —$SO_3H$ and salts thereof; —$CONH_2$, —$CONHCH_2OH$ or $(OCH_2CH_2)_nOH$;

$Q^-_2$ is —$COO^-$;

m is 2 to 10;

n is 1 to 10 and p and q are 1 to 500.

Preferably, $L_1$ is —$CH_2$—, —$CH_2CH_2$—, —CH=CH— and —$CH_2CH_2CONHC(CH_3)_2CH_2$—; AND $L_2$ IS —$CH_2$—; $Q_1$ is —COOH and —$SO_3H$ or a salt thereof and m is 2 and p, q and r are 1 to 100.

Segment C are segments of formula IIIa and IIIb containing a hydrophobic group

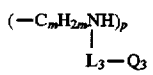

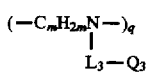

wherein $L_3$ is —CO— or —$SO_2$—;

$Q_3$ is a straight or branched hydrocarbon group with 6 to 18 carbon atoms;

m is 2 to 10 and p and q are 0 to 100.

Preferably, $L_3$ is zero or —CO—; $Q_3$ is straight alkyl with 8 to 18 carbons, m is 2 and p and q is 0 to 50.

The instant FS-additives can readily be derived in quantitative or near quantitative yield from polyamines containing segments of formula IVa, IVb and IVc and esters or acid halides or perfluoroalkyl groups containing carboxylic and sulfonic acids of formula V and VI, and reactants of formula VIIa, VIIb and VIII.

Polyamines containing segments of formula IVa, IVb and IVc

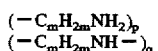

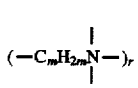

suitable for the synthesis of the instant FS-additives must have at least a combined total of three primary or secondary amino groups.

Suitable polyamines are commercially available aliphatic polyamines as described in Kirk Othmer, *Concise Encyclopedia of Chemical Technology*, John Wiley and Son, p. 350–351, (1985) and include:

| | |
|---|---|
| diethylenetriamine (DETA) | $H_2NCH_2CH_2NHCH_2CH_2NH_2$ |
| triethylenetetramine (TETA) | $H_2N(CH_2CH_2NH)_2CH_2CH_2NH_2$ |
| tetraethylenepentamine (TEPA) | $H_2N(CH_2CH_2NH)_3CH_2CH_2NH_2$ |
| pentaethylenehexamine (PEHA) | $H_2N(CH_2CH_2NH)_4CH_2CH_2NH_2$ |
| aminoethylpiperazine (AEP) | $NH_2CH_2CH_2N(CH_2CH_2)_2NH_2$ |
| iminobispropylamine (IBPA) | $H_2N(CH_2)_3NH(CH_2)_3NH_2$ |

Higher molecular weight polyamines can be derived from the above amines, as well as from ethylene diamine, propylene diamine, 1,3-diamino propane and hexamethylene diamine, by reaction with difunctional halohydrins or with diesters and with divinyl compounds as described in U.S. Pat. No. 2,977,245. Preferred polyamines are so-called polyethyleneimines or alkyl substituted polyethyleneimines which are derived by the homopolymerization of ethyleneimine and its derivatives using acid catalysts such as HCl, $BF_3$ and the like.

Examples of such monomers yielding polyethyleneimines useful for the synthesis of the instant additives are ethyleneimine; 1,2-propyleneimine, 1,2-butyleneimine, 2,2-dimethylethyleneimine; 2,3-butyleneimine and 2,2-dimethyl-3-n-propylethyleneimine as described in the "*Journal of American Chemical Society*," Vol. 57, p. 2328 (1935) and "*Journal of Organic Chemistry*," Vol. 9, p. 500 (1944).

Most important of the above polyimines are polyethyleneimines (PEIs), which are available commercially with molecular weights ranging from 300 to 70,000 and contain approximately 25% primary amino groups, 50% secondary amino groups and 25% tertiary amino groups. The units forming PEI are (—$CH_2CH_2NH_2$), (—$CH_2CH_2NH$—) and

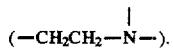

The polymer structure of PEI can also be described as a highly branched polyamine containing polymer segments such as:

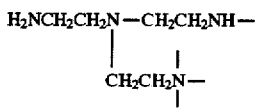

Preferred polyethyleneimines can have molecular weights ranging from 600 to 70,000 and depending on the specific performance properties desired, blends or polyethyleneimines with different average molecular weights can also be utilized.

Suitable perfluoroalkyl carboxylic and sulfonic acids of type V and VI

and esters and acid halides thereof wherein $R_f$ and E are as defined previously are well known and extensively described in the patent literature as for instance listed in U.S. Pat. Nos. 4,472,286 and 5,085,786 and include for example

| | |
|---|---|
| $R_fCOOH$ | $R_fSO_3H$ |
| $R_f(CH_2)_{1-20}COOH$ | $R_f(CH_2)_{1-20}SO_3H$ |
| $R_fSO_2N(C_2H_5)CH_2COOH$ | $R_fCH_2CH_2OCH_2CH_2SO_3H$ |
| $R_f(CH_2)_{1-12}S(CH_2)_{1-17}COOH$ | $R_fSO_2NHCH_2C_6H_4SO_3H$ |
| | $R_fCH_2CH_2SCH_2CH_2CONHC(CH_3)_2CH_2SO_3H$ |

Preferred $R_f$-esters and $R_f$-acid halides used for the synthesis of the instant FS-additives are the ones either commercially available or which can be derived in high yields from commercially available $R_f$-precursors. Commercially available $R_f$-acid halides are $R_f$-carboxylic acid and sulfonic acid fluorides produced via electrofluorination and $R_f$-acids obtained via oxidation of $R_f$-ethyl iodides. $R_f$-esters which are obtained in very high yield from $R_f$-ethyl iodides and commercially available mercapto esters or by the addition of commercially available $R_f$-ethyl mercaptans to acrylic esters, using in both instances bases as catalysts as shown in the equations below:

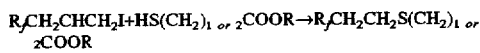

or

wherein R is lower alkyl and $R_f$ is as defined previously. Instead of the above mercapto-esters, diesters such as $HS(CH_2)_{1\ or\ 2}COO-CH_2CH_2-OCO(CH_2)_{1\ or\ 2}SH$ can also be utilized as described in the experimental part.

Reactants of formula VII are compounds with hydrophilic group as well as a group reacting readily with primary and secondary amino groups and optionally with tertiary amino groups present in polyamines containing segments of formula IVa, IVb and IVc.

The reaction of primary and secondary amines with aldehydes and ketones, alkyl halides, isocyanates and thioisocyanates, activated double bond sites, epoxy compounds, cyanamide and guanidine or urea and the like, acids and anhydrides and acyl halides, is well known to the one skilled in the art.

Similarly, it is well known that tertiary amino groups can be converted into betaines via carboxalkylation with halogen carboxylic acids and salts thereof or into sulfobetaines via sulfalkylation with sultones such as propane sultone or butane sultones.

Of the above possibilities to introduce hydrophilic groups to obtain segments of formula IIa, IIb and IIc the following reactants were found to be the preferable ones;

Hydrophilic group containing alkyl halides of formula VIIa $$X-L_1Q_1 \qquad (VIIa)$$

wherein

X is halogen and preferably Cl, $L_1$ is alkylene with 1 to 4 carbons and preferably $-CH_2-$ and $Q_1$ is a salt of $-COOH$ and preferably $-COONa$ will yield segments of formula IIa, IIb and IIc, the most preferred reactant VIIa being monochloro sodium acetate.

Hydrophilic group containing activated double bond compounds such as maleic anhydride and acrylates and methacrylates of formula VIIb

wherein $L_1$ is zero or a bivalent linking group and $Q_1$ is $-COOH$ and $-SO_3H$ and salts thereof, $-CONH_2$, $-CONHCH_2OH$ or $-(OCH_2CH_2)_nOH$ and n is 1 to 10 will yield segments of formula IIa and IIb. The most preferable reactants being acrylic acid, maleic anhydride and acrylamide.

Furthermore, it is possible to obtain segments of formula IIa and IIb wherein $-L_1-Q_1$ is $-COCH_2CH_2COOH$ and salts thereof by reaction of the primary and secondary amino groups with anhydrides such as succinic anhydride or to obtain formula IIa and IIb segments wherein $-L_1Q_1$ is $-COCH=CHCOOH$ and salts thereof by the reaction with maleic anhydride.

Reactants of formula VIII are compounds with a non-fluorochemical hydrophobic group as well as a group reacting with primary and secondary amino groups as outlined for reactants of formula VIIa and VIIb.

However, because of commercial availability, the preferred reactants of formula VIII are lower alkyl esters of longchain alkanoic acids.

$$R-O-L_3-Q_3 \qquad (VIII)$$

wherein

R is alkyl with 1 to 4 carbons $L_3$ is $-CO-$ and $Q_3$ is straight or branched alkyl with 12 to 18 carbons.

The synthesis of the instant FS-additives is carried out by using well known reaction conditions, solvents and reactants as described.

The preferred synthesis procedure consists of reacting in a first step one mole of a polyamine with a select number of moles of an $R_f$-ester as defined or with a blend of an $R_f$-ester and a fatty acid ester, if it is desired to incorporate a non-fluorochemical hydrophobic group into the FS-additive to be synthesized.

The fist step is carried out by heating the reactants in a solvent such as isopropanol in the absence or the presence of a catalyst such as sodium ethoxide and sodium borohydride to 80° to 110° C. for several hours under nitrogen and good stirring conditions, until IR-analysis shows that the ester-bond has completely disappeared and the amide-formation is complete. After conversion is completed, the isopropanol and the alcohol formed is distilled off and the resulting polyamine-amide adduct, a brownish viscous liquid is charged slowly into an aqueous solution containing a select number of moles of the hydrophilic group containing reactant of formula VIIa or VIIb keeping reaction temperature at 40° to 70° C. until addition is completed, followed by heating the reaction mixture for several hours to about 70°–80° C. Then a 50% sodium hydroxide solution is added in amounts to bring the pH to about 7.5. The resulting solution with a solids content ranging from 30 to 40% can be used as an FS-additive without any further purification.

Alternatively, one can add the aqueous solution of the hydrophilic group containing reactant slowly into the addition product (step 1) of the polyamine and the $R_f$-ester.

Since it is known how many primary, secondary and tertiary amino groups are present per mole of polyamine, one also knows, how many moles of reactants can be added and be added in such a ratio of perfluoroalkyl group, hydrophilic and hydrophobic group containing reactants, that the end product will be water soluble, which means having a solubility of at least 0.1% in water at 25° C. In order to determine the optimum composition of the instant water soluble FS-additive, different FS-additives have to be evaluated as additives in select AFFF and AR-AFFF agents.

EXPERIMENTAL PART

The following examples are illustrative of the various representative embodiment of this invention and are not to be interpreted as limiting in scope of the appended claims.

In these examples, references are made to specifications used by the industry to evaluate the performance and efficiency of the instant foam stabilizers. More specifically, the examples refer to the following specifications and laboratory test methods:

1. Surface Tension and Interfacial Tension: According to ASTM C-1331-56.

2. Laboratory Film Spreading and Burnback Test: This test is carried out to determine film formation and film speed of AFFF premixes on cyclohexane as well as film life.

A 100×20 mm pyrex petri dish is placed over a dark, wet surface, so that good visual observation is possible. 50 ml of cyclohexane solvent is added to the petri dish. A 0.5 inch long stainless steel wood screw, pointing upwards, is placed in the center of the dish. The timer is started and simultaneously 3 ml of AFFF premix are added dropwise from a capillary pipette in one-second intervals onto top of screw.

When the surface of the solvent is completely covered with the film, the time of seal is recorded. The timer is left running and the screw is removed carefully so as not to disturb the film layer. With a lighter, the surface is tested for breakup of the seal. If the seal is broken, the solvent will ignite. The flames are extinguished by placing a cardboard over the dish. The timer is stopped and the time or breakup is recorded.

3. Laboratory Foam Expansion and Drain Time Test: 100 ml of an AFFF premix to be tested is prepared with either tap or artificial seawater (ASTM D1141). 100 ml of AFFF premix is poured into a Waring blender. At medium speed, the AFFF solution is blended for 60 seconds. The generated foam is poured into a graduated 1000 ml cylinder, and a spatula is used to remove any residual foam in the blender cup. The foam height is recorded and the foam expansion ratio is calculated by dividing foam volume (ml) by foam weight (g).

The time which passes between the time the blender was stopped and the drain in the graduated cylinder reaches (a) 25.0 ml and (b) 50 ml is recorded. These times are called ¼ and ½ drain times.

4. Laboratory IPA Foam Stability Test: This test is carried out to determine the stability of foam generated from AFFF and AR-AFFF agents in contact with hot isopropanol. Alternatively, this test can also be carried out with other polar solvents, such as acetone.

Virgin IPA, heated to 70° C. is poured into a 150 mm wide and 75 mm high pyrex dish to an IPA level of approximately one inch. To the hot IPA is immediately poured all of the foam generated from 100 ml of a 3% AFFF or AR-AFFF agent premix, by blending the premix solution for 60 seconds on medium speed in a Waring blender. The time which passes between the time the foam is poured onto the hot IPA and the time when 50% of the surface area is visible is called the 50% foam collapse time and the time required until 100% of the surface area is visible is called the 100% foam collapse time.

5. Modified UL 162 Fire Test: This test is carried out to determine the efficiency of aqueous film forming foams to control and extinguish either isopropanol or acetone fires on a scale suitable for developmental agents.

15 liters of 99% isopropanol or acetone is placed into a round pan that is 2.69 ft$^2$ in area and 4½" deep, and ignited. After one minute of free burning a foam discharge delivering 0.269 gpm's of solution is directed onto the far wall of the fire pan in a solid stream application for two minutes with a Type II Fixed Nozzle producing a foam quality that conforms to UL 162 5th edition paragraphs 15–15.9. One minute after the three minute foam application, a jet (5/32" diameter) of propane gas is ignited and discharged over the center of the foam blanket at the rate of 100 cc/m. metered by a full view Rotameter, Model 8900D as manufactured by Brooks Instrument Div. Emerson Electric Co., King of Prussia, Pa. or equivalent.

The impingement of the propane flame commences two inches above the top of the tank and shoots downwardly over the foam blanket.

The propane flame is removed 30 seconds after the foam under the propane flame has collapsed and the fuel surface under the flame is visible. The burnback test is continued until 20% of the surface area of the test pan is on fire.

In this test, the following is measured or timed: Air, agent premix and initial fuel temperature; foam expansion and quarter drain time (tested separately with same nozzle as used in fire test), time required to cover 25, 50 and 75% of pan surface with foam; time required to achieve 90% and 98% control of the fire and total extinguishment time. Furthermore, the time required from start of the burnback test until the fuel surface is exposed under the flame and time required until 20% of surface area is reinvolved in flames is measured.

In the following examples, the following commercial raw materials were used for the synthesis of intermediates and of the instant foam stabilizers:

Perfluoroalkylethyl iodides with perfluoroalkyl groups having from 6 to 12 carbon atoms are available from Atochem under the Foralkyl name, (Foralkyl El 6, El 8, El 6N and El 10N; from DuPont under the Zonyl name (Zonyl TELB, TELB-L and TELB-N) and Hoechst-Celanese under the Fluowet name (Fluowet El-600, El-612 and El-812).

Perfluoroalkylethyl mercaptans with $R_f$-groups as present in the above perfluoroalkylethyl iodides are available from Atochem under the Foralkyl name (Foralkyl EM 6, EM 8, EM 6N, EM 8N and EM 10N).

Thioglycolates and mercaptopropionates, such as n-butyl thioglycolate and glycol dimercaptopropionate are available from the Evans Chemetics unit of Hampshire Chemical Corporation.

Esters of perfluorocarboxylic acids such as methyl perfluorooctanoate, and methyl perfluorononanoate are available from PCR, Inc., and perfluoro alkane sulfonyl fluorides such as perfluorooctane sulfonyl fluoride are available from the 3M Company.

Polyethylenemines with molecular weights ranging from 300 to 70,000 are available from Nippon Shokubai Co. under the Epomin name (Epomin SP-003, SP-006, SP-018, SP-200 and P-1000).

Polyamines such as diethylenetriamine (DETA), triethylenetetramine (TETA), tetraethylenepentamine (TEPA), pentaethylenehexamine (PEHA), iminobispropylamine (IBPA) are commodity chemicals and available from a number of companies.

In order to show the efficiency of the instant foam stabilizers and their impact when added to AFFF and AR-AFFF agents, commercial AFFF and AR-AFFF agents by the leading U.S. agent producers were selected as model agents, namely Ansulite 3% AFFF and Ansulite 3×3 AR-AFFF agents produced by Ansul Fire Protection; Aer-O-Lite 3% AFFF and Universal Gold 3×3 AR-AFFF agents produced by National Foam Inc., and Light Water FC-203CS 3% AFFF and Light Water FC-603F 3×3 AR-AFFF agents produced by the 3M Company. Also used were developmental agents produced by the Dynax Corporation.

The following examples 1 to 6 show the synthesis of $R_f$-esters which were used as intermediates for the synthesis of the instant foam stabilizers. The reaction of iodides with mercaptans yielding sulfides as well as the addition of mercaptans to unsaturated esters using base catalysts is well known to the one skilled in the art giving yields which are almost quantitative, making the use of crude $R_f$-esters possible without any further purification. In Table 1, the structures of $R_f$-esters A-1 through A-6 are presented, as well as the $R_f$-distribution in these esters and in the $R_f$-ethyl iodides and $R_f$-ethyl mercaptan raw materials.

Also listed in Table 1 are $R_f$-esters and a $R_f$-sulfonyl fluoride which are available commercially.

EXAMPLE 1

$$C_6F_{13}CH_2I+$$
$$HSCH_2COOC_4H_9 \rightarrow C_6F_{13}CH_2CH_2SCH_2COOC_4H_9+HI$$

To a 3-neck flask equipped with stirrer, thermometer, dropping funnel and reflux condenser were charged 474 gm (1.0 mole) of $C_6F_{13}CH_2CH_2I$, 163 gm (1.1 mole) of n-butyl thioglycolate, 37 gm (0.37 mole) of triethylamine and 120 gm of butyl acetate. While stirring, the reaction mixture was heated to 55° C., allowed to exotherm to 70° and kept at 70°–75° C. for 3 hours. After this heating period, another 74 gm (0.74 moles) of triethylamine were added over a two-hour period while the reaction temperature was kept at 70° to 75° C. Upon completion of the addition of the triethylamine, the temperature was raised to 100° C. and kept overnight (12 hours) at this temperature. GC analysis showed, that the content of $C_6F_{13}CH_2CH_2I$ in the reaction mixture had dropped to less than 1.0%. The reaction mixture was cooled to 50° C. and 200 ml of deionized water was added. After stirring for 30 minutes and letting the reaction mixture stand for another 30 minutes, the organic layer was separated from the aqueous layer. The organic layer was once more washed with 200 ml of deionized water. After separation of the aqueous from the organic layer, the organic layer was transferred to a distillation flask and under vacuum of 25 to 100 mg Hg, the volatiles, butyl acetate, small amounts of $C_6F_{13}CH=CH_2$ byproduct, unreacted $C_6F_{13}CH_2CH_2I$, triethylamine and water were distilled off by raising the distillation batch temperature to 130°, until distillation did come to a halt. A total of 493 gm (99.6% yield) of butyl perfluorohexylethylthioglycolate was obtained as a slightly off-white viscous liquid, which was used without any further purification for the reaction with oligomeric and polymeric amines of this invention.

EXAMPLES 2 TO 5

Using the synthesis method as described in Example 1, the following perfluoroalkylethylthioglycolate esters A-2, A-3, A-4 and A-5 were synthesized from the following perfluoroalkylethyl iodides having an $R_f$-distribution as shown in Table 1, and butyl thioglycolate and glycol dimercaptopropionate:

$$R_fCH_2CH_2I+$$
$$HSCH_2COOC_4H_9 \rightarrow R_fCH_2CH_2SCH_2COOC_4H_9$$
(A-2, A-3)

$$2\ R_fCH_2CH_2I+(HSCH_2COOCH_2)_2 \rightarrow$$
$$(R_fCH_2CH_2SCH_2COOCH_2)_2\ \text{(A-4 and A-5)}$$

EXAMPLE 6

$$R_fCH_2CH_2SH+$$
$$CH_2=CHCOOCH_3 \rightarrow R_fCH_2CH_2SCH_2CH_2COOCH_3$$

To a 3-neck flask equipped with stirrer, dropping funnel, thermometer and reflux condenser were added 63.6 g (0.74 moles) of methyl acrylate and 7.0 g (0.07 moles) of triethylamine. At room temperature and under stirring, a total of 377.6 g (0.716 moles) of perfluoroalkylethyl mercaptan, having a $R_f$-distribution as shown in Table 1, were added over a period of one hour, during which the exotherm raised the batch temperature to 58° C. The conversion after completion of addition as determined by GC-analysis was approximately 70%. After the reaction mixture was kept at 60° C. overnight, GC-analysis showed 100% conversion. The product (456 g, 98.5% yield) was a white, semi-solid compound at room temperature and was used for the reaction with oligomeric and polymeric amines of this invention without any further purification.

The following examples 7 to 20 show the synthesis of select FS-additives derived from commercially available polyamines, while examples 21 to 40 show the laboratory

TABLE 1

| | | | $R_f$-Distribution, % | | | |
|---|---|---|---|---|---|---|
| Example | A-# | Formula | $C_6F_{13}$ | $C_8F_{17}$ | $C_{10}F_{21}$ | $\geq C_{12}F_{25}$ |
| 1 | A-1 | $R_fCH_2CH_2SCH_2COOC_4H_9$ | 98.0 | 2.0 | — | — |
| 2 | A-2 | " | 38–46 | 28–34 | 13–17 | 10 max. |
| 3 | A-3 | " | 10–20 | 50–56 | 18–22 | 12 max. |
| 4 | A-4 | $(R_fCH_2CH_2SCH_2COOCH_2)_2$ | 38–46 | 28–34 | 13–17 | 10 max. |
| 5 | A-5 | " | 10–20 | 50–56 | 18–22 | 12 max. |
| 6 | A-6 | $R_fCH_2CH_2SCH_2CH_2COOCH_3$ | <1.0 | 62 | 25.7 | 8.6 |
| — | A-7 | $C_7F_{15}COOCH_3$ | — | — | — | — |
| — | A-8 | $C_8F_{17}COOCH_3$ | — | — | — | — |
| — | A-9 | $C_8F_{17}SO_2F$ | — | — | — | — | evaluations of AFFF and AR-AFFF agent premixes containing such select FS-additives. Examples 41 and 42 show fire tests carried out with polysaccharide-free AR-AFFF agents containing FS-additives and using tap and sea water for the preparation of agent premixes and isopropanol and acetone as polar solvent fuels.

EXAMPLE 7

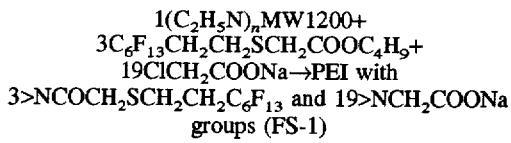

$1(C_2H_5N)_nMW1200+$
$3C_6F_{13}CH_2CH_2SCH_2COOC_4H_9+$
$19ClCH_2COONa \rightarrow PEI$ with
$3>NCOCH_2SCH_2CH_2C_6F_{13}$ and $19>NCH_2COONa$
groups (FS-1)

To a 3-neck flask equipped with stirrer, thermometer and reflux condenser were charged 200 g (0.166 mole) of polyethyleneimine (Epomin P012) with an average mole weight of 1200; 247 g (0.5 mole) of n-butyl perfluorohexylethylthioglycolate (A-1) and 110 g of isopropanol. The reactants were mixed and when homogeneous, 6.5 g of a 20% solution of sodium ethoxide in ethanol and 1.3 g of sodium borohydride were added to the reaction mixture. Upon inertion of the reactor with nitrogen, the reaction mixture was heated to 105° to 115° C. and was kept at this temperature for 4 hours by refluxing the isopropyl alcohol during the first one hour period and by distilling off the isopropyl alcohol during the remaining three-hour period. An IR taken after the four-hour period showed that the amide formation was completed and the ester band at 1725–1735 cm$^{-1}$ had disappeared. Vacuum was applied and residual volatiles were distilled off at 105° C. and a vacuum of 100 mm Hg.

The resulting brown viscous liquid was cooled to 80°–90° C. and over a 30-minute period charged into a flask containing a solution of 375 g (3.22 mole) of sodium chloroacetate in 900 g of water kept at a temperature of 50° C., controlling the exotherm by cooling the flask so that a temperature between 45° and 55° C. was maintained during the addition. The 3-neck flask which did contain the viscous $R_f$-ester polyethylenemine adduct was rinsed with 150 g of water and this rinse was added to the flask with the sodium chloroacetate reaction mixture. After addition of this rinse out, the reaction mixture was kept at 65° to 70° C. for four hours. Two hours into this holding period, 24.9 g of a 50% sodium hydroxide solution was added to raise the pH to 7.5. A total of 1845 g (96% yield) of a brown solution with an actives content of 35% was obtained which was used without any further purification.

EXAMPLE 8

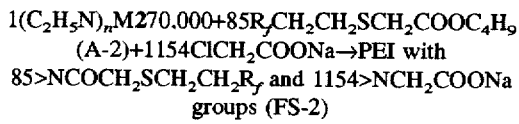

$1(C_2H_5N)_nM270.000+85R_fCH_2CH_2SCH_2COOC_4H_9$
$(A-2)+1154ClCH_2COONa \rightarrow PEI$ with
$85>NCOCH_2SCH_2CH_2R_f$ and $1154>NCH_2COONa$
groups (FS-2)

To a 3-neck flask equipped with a stirrer, thermometer and reflux condenser were charged 13 g (0.0227 moles) of butyl perfluoroalkylethylthioglycolate A-2, 61.9 g (0.00027 moles) of a 30% aqueous solution of polyethyleneimine (Epomin P-1000) with an average molecular weight of 70.000 and 80 g of isopropanol. The reaction mixture was heated to 100° C. and kept at reflux overnight for a total of 18 hours. IR analysis showed only trace amounts of ester groups. A total of 100 ml of IPA/water were distilled off and a total of 70.2 g of a yellowish solution was obtained. 200 g of water and 100 g of propylene glycol were added, followed by the addition of 34 g (0.3 moles) of sodium chloroacetate at 40° C. The reaction mixture was kept at 75°–80° C. for 4 hours. A foaming mass was obtained. Addition of 100 g of butyl cellosolve did not brake the foam. Upon standing for 3 days, the foam had collapsed and a total of 445 g of a brown foam stabilizer solution with an actives content of 12.3% was obtained which was used without any further purification.

TABLE 2

| Example | Foam Stabilizer Nr. | Mol. Weight of PEI[1] | $R_f$-Ester | Hydrophile | Mole Ratios of Reactants | % Actives in Solution |
|---|---|---|---|---|---|---|
| 7 | FS-1 | 1,200 | A-1 | ClCH$_2$COONa | 1:3:19 | 34.7 |
| 8 | FS-2 | 70,000 | A-2 | " | 1:85:1154 | 12.3 |
| 9 | FS-3 | 1,200 | " | " | 1:2:20 | 36.4 |
| 10 | FS-4 | " | A-6 | " | 1:2:20 | 40.0 |
| 11 | FS-5 | " | A-2 | " | 1:1.5:21 | 35.4 |
| 12 | FS-6 | 1,800 | A-1 | " | 1:3:28 | 36.9 |
| 13 | FS-7 | " | " | CH$_2$=CHCOONa | 1:3:28 | 43.8 |
| 14 | FS-8 | 10,000 | " | ClCH$_2$COONa | 1:8:167 | 20.3 |

[1]Polyethyleneimines (PEIs) used are the following Epomines (SP and P Series), having the following molecular weights and numbers of primary, secondary and tertiary amino groups:

| Epomin Nr. | MW | —NH$_2$ | —NH— | —N< | Total N |
|---|---|---|---|---|---|
| SP-012 | 1,200 | 7 | 14 | 7 | 28 |
| SP-018 | 1,800 | 10.5 | 21 | 10.5 | 42 |
| SP-200 | 10,000 | 58 | 116 | 58 | 232 |
| SP-1000 | 70,000 | 406 | 813 | 406 | 1,625 |

EXAMPLE 9 TO 14

Using the synthesis procedure and the catalysts as described in Example 7, Epomin polyethyleneimines were reacted with $R_f$-esters (step 1) and then either sodium chloroacetate or acrylic acid (step 2) in mole ratios as indicated in Table 2 yielding foam stabilizers B-3 to B-8. In these reactions, the polyethylenemine/$R_f$-ester adduct was mixed in one step with the aqueous sodium chloroacetate solution, rather than added over a period of time, since controlling the exotherm on a small synthesis scale was no problem. Because foaming in step 2 was a problem, propylene glycol was added to break the foam which was only marginally successful and did lead to more diluted foam stabilizer solutions as indicated in Table 2. All foam stabilizer solutions obtained with active contents as shown in Table 2 were light to dark brown in color.

EXAMPLE 15 TO 17

Using the synthesis procedure as described in Example 7, but using in step 2 propylene glycol as solvent and triethanolamine as a catalyst and solubilizer, foam stabilizers were prepared from polyamines, $R_f$-esters and hydrophiles as shown in Table 3, having the following idealized structures:

EXAMPLE 15 (FS-9)

[$R_f$CH$_2$CH$_2$SCH$_2$CONHCH$_2$CH$_2$NCH$_2$]$_2$
         |
         CHCOOH.N(CH$_2$CH$_2$OH)$_3$
         |
         CH$_2$COOH.N(CH$_2$CH$_2$OH)$_3$

EXAMPLE 16 (FS-10)

[$R_f$CH$_2$CH$_2$SCH$_2$CONHCH$_2$CH$_2$NCH$_2$]$_2$
         |
         COCH$_2$CH$_2$COOH.N(CH$_2$CH$_2$OH)$_3$

EXAMPLE 17 (FS-11)

[$R_f$CH$_2$CH$_2$SCH$_2$CONHCH$_2$CH$_2$NCH$_2$]$_2$NCOCH$_2$CH$_2$COOHN.N(CH$_2$CH$_2$OH)$_3$
         |
         COCH$_2$CH$_2$COOH.N(CH$_2$CH$_2$OH)$_3$

TABLE 3

| Ex. | Polyamine | $R_f$-Ester | Hydrophile | Mole Ratio[1] | % Solids in Solution |
|---|---|---|---|---|---|
| 15 | H$_2$N(CH$_2$CH$_2$NH)$_2$CH$_2$CH$_2$NH$_2$ | A-4 | MA[2] | 1:1:2 | 28.6% |
| 16 | H$_2$N(CH$_2$CH$_2$NH)$_2$CH$_2$CH$_2$NH$_2$ | A-5 | SA[3] | 1:1:1.9 | 36.9% |
| 17 | H$_2$N(CH$_2$CH$_2$NH)$_3$CH$_2$CH$_2$NH$_2$ | A-4 | SA | 1:1:3 | 38.8% |

[1]Mole Ratio of Polyamine to $R_f$-Ester to Hydrophile.
[2]MA = Maleic anhydride.
[3]SA = Succinic anhydride.

EXAMPLES 18 TO 20

Using synthesis methods as described for examples 7 through 17, foam stabilizers can be derived from esters of perfluorocarboxylic acids A-7, A-8 and acid sulfonyl fluoride A-9, polyamines and hydrophiles such as sodium chloroacetate, maleic anhydride, and succinic anhydride having structures as shown below:

EXAMPLE 18 (FS-12)

(C$_7$F$_{15}$CONHCH$_2$CH$_2$NCH$_2$)$_2$
         |
         CHCOOH.N(CH$_2$CH$_2$OH)$_3$
         |
         CH$_2$COOH.N(CH$_2$CH$_2$OH)$_3$

EXAMPLE 19 (FS-13)

(C$_8$F$_{17}$CONHCH$_2$CH$_2$NCH$_2$)$_2$
         |
         COCH$_2$CH$_2$COOH.N(CH$_2$CH$_2$OH)$_3$

EXAMPLE 20 (FS-14)

C$_8$F$_{17}$SO$_2$NH(CH$_2$CH$_2$N)$_3$CH$_2$CH$_2$NHCH$_2$COONa
         |
         CH$_2$COONa

EXAMPLES 21-30

To determine the efficiency of the instant foam stabilizers, AR-AFFF agent premixes were prepared by mixing 3 parts of Ansulite 3×3 and alternatively 3 parts of Light Water FC603F with 0.5 parts of an aqueous solution containing 3% by weights foam stabilizer solids and 96.5 parts of tap water. The results in Table 4 show that the foam collapse time on hot IPA was increased significantly by all of the instant foam stabilizers evaluated even though only 0.015% solids of foam stabilizer (0.5×0.03) were present in the premixes evaluated.

TABLE 4

| | | IPA Foam Stabilizer Collapse Time in Minute/Seconds | | | |
|---|---|---|---|---|---|
| | Foam Stabilizer | Ansulite 3 × 3 | | Light Water FC-603F | |
| Example | Number | 50% | 100% | 50% | 100% |
| 21 | None | 2:46 | 3:05 | 6:21 | 7:32 |
| 22 | FS-1 | 28:40 | >30:00 | 27:31 | 28:05 |
| 23 | FS-3 | 19:18 | 28:59 | 24.23 | >30:00 |
| 24 | FS-4 | 18:29 | 21:04 | 18:11 | 21:33 |
| 25 | FS-6 | 11:31 | 14:03 | 26:15 | 29:55 |
| 26 | FS-7 | 9:00 | 11:29 | 22:27 | 25:29 |
| 27 | FS-8 | —[1] | — | —[1] | — |
| 28 | FS-9 | 9:59 | 13:53 | 10:36 | 21:26 |
| 29 | FS-10 | 25:16 | >30:00 | 14:26 | 21:45 |
| 30 | FS-11 | 10:55 | 13.37 | 12:51 | 16:45 |

[1]Precipitate formed, not evaluated.

EXAMPLES 31-35

In order to show how the instant foam stabilizers can improve the IPA foam stability of AR-AFFF agents as a function of the amount of foam stabilizer added, agent premixes were prepared by blending 3 parts of Universal Gold 3% AR-AFFF agent with 0.25 to 1.0 parts of a solution containing 3% by weight of FS-3 foam stabilizer solids. The IPA foam stability tests carried out with these premixes gave results as shown in Table 5, indicating 50% foam collapse time increased from 37 seconds to 27 minutes.

TABLE 5

| | | IPA Collapse Time Minutes | |
|---|---|---|---|
| Example | AR-AFFF Premixes | 50% | 100% |
| 31 | Universal Gold 3% | 0:37 | 0:51 |
| 32 | Universal Gold + 0.25% FS-3 | 8:19 | 12:54 |
| 33 | Universal Gold + 0.50% FS-3 | 14:57 | 28:26 |
| 34 | Universal Gold + 0.75% FS-3 | 22:63 | 42:20 |
| 35 | Universal Gold + 100% FS-3 | 27:19 | 53:41 |

EXAMPLES 36 TO 40

In order to demonstrate that AR-AFFF agents with lower polysaccharide contents and lower viscosity can be prepared with the help of the instant foam stabilizers, the following was carried out:

It was established that Universal Gold 3%, a 3×3 AR-AFFF agent and Aer-O-Lite 3%, a 3% AFFF agent, both produced by National Foam, Inc., were compatible when mixed in ratios from 80/20 to 40/60 of Aerowater Gold 3% to Aer-O-Lite 3% yielding agents with Brookfield viscosities as shown in Table 6.

It was found that addition of small amounts of foam stabilizers (0.25 to 1.0% FS-Solids) did not affect the above viscosities. Agent premixes were prepared by blending 3 parts of the above agent compositions and 3 parts of a solution containing 0.75% solids of foam stabilizer FS-3, with 94 parts of tap water.

As shown in Table 6, these premixes were evaluated and did yield the following results:

Most importantly, the IPA collapse times were significantly increased when compared with the IPA collapse time of Universal Gold 3% alone. However, IPA collapse times were increased less the higher the amount of Aer-O-Lite was in the agent blend and the lower the content of Universal Gold 3%. Foam drainage times decreased with amounts of Aer-O-Lite 3% greater than 20% while surface and interfacial tensions increased slightly with increasing amounts of Aer-O-Lite 3% in the premix.

TABLE 6

Laboratory Evaluation of Agent Premixes

| | Examples | | | | |
|---|---|---|---|---|---|
| | 36 | 37 | 38 | 39 | 40 |
| Universal Gold 3% (AR-AFFF) | 100 | 100 | 80 | 60 | 40 |
| Aer-O-Lite 3% AFFF | — | — | 20 | 40 | 60 |
| Foam Stabilizer FS-3[1] | No | Yes | Yes | Yes | Yes |
| Surface Tension, dynes/cm | 17.1 | 17.3 | 17.5 | 17.6 | 17.7 |
| Interfacial Tension, dynes/cm | 2.1 | 2.2 | 2.2 | 2.3 | 2.4 |
| Foam Expansion | 7.1 | 7.1 | 6.7 | 7.5 | 9.0 |
| 25% Drain Time, Minutes | 12:02 | 11:11 | 13:22 | 10:52 | 8:58 |
| 50% Drain Time, Minutes | 15:28 | 15:37 | 17:54 | 13:18 | 12:15 |
| IPA 50% Collapse Time, Minutes | 0:37 | 22:38 | 7:15 | 2:19 | 0:15 |
| IPA 100% Collapse Time, Minutes | 0:51 | 42:20 | 14:58 | 6:44 | 1:25 |
| Viscosity, cps, Brookfield[2] | 2880 | 2880 | 2227 | 1420 | 748 |

[1] 0.75% Solids FS-3 in agent concentrate, 0.015% Solids in agent premix.
[2] Brookfield LVT, 30 RPM, Spindle 3.

EXAMPLES 41 AND 42

A Dynax 3% AFFF agent (DX-1) with a fluorine content of 0.7% and performance properties as shown in Table 7 was reformulated in such a way that in addition to all components present in DX-1, 1.4% solids of foam stabilizer FS-1 and 1.15% solids of foam stabilizer FS-2 were incorporated into the 3% concentrate. The comparative laboratory evaluations in Table 7 show that incorporation of the foam stabilizers did only very marginally affect surface and interfacial tensions, did slightly decrease the film speed, but more importantly did increase both foam expansion and drain times and most importantly did provide excellent IPA foam resistance as the very long 50% and 100% IPA collapse times show in both tap and sea water.

In order to show the efficiency of this "Newtonian" 3×3 AR-AFFF agent, modified UL 162 2.69 sq. ft. fire tests were carried out with tap and sea water on IPA and acetone fires.

As the test results in Table 8 show, excellent fire control and extinguishment times were obtained on both IPA and acetone fires.

TABLE 7

Laboratory Evaluations of DX-1 and DX-2 Agents

| | Examples | | | |
|---|---|---|---|---|
| | 41 | | 42 | |
| | Dynax 3% | | Dynax 3 × 3 | |
| Properties of AFFF and | AFFF DX-1 | | AR-AFFF DX-2 | |
| AR-AFFF Premixes | Tap | Sea | Tap | Sea |
| Surface Tension, dynes/cm | 17.1 | 17.6 | 18.3 | 18.2 |
| Interfacial Tension, dynes/cm | 1.6 | 1.4 | 1.8 | 1.6 |
| Foam Expansion Ratio | 5.2 | 5.2 | 6.3 | 6.0 |
| ¼ Drain Time, min./sec. | 4:58 | 4:07 | 7:39 | 8:05 |
| ½ Drain Time, min./sec. | 6:23 | 5:07 | 10:38 | 11:01 |
| Seal Time, min./sec. | 0:04 | 0:04 | 0:12 | 0:10 |
| Seal Breakup, min./sec. | >30:00 | >30:00 | >30:00 | >30:00 |
| IPA 50% Collapse min./sec. | 0:12 | 0:12 | 97:05 | 19:51 |
| IPA 100% Collapse min./sec. | 0:12 | 0:12 | 188:00 | 53:51 |

TABLE 8

Comparative Modified UL 162 Fire Tests

| | | Tap Water Premix | | Sea Water Premix | |
|---|---|---|---|---|---|
| Air Temperature | 85° F. (°C.) | | | | |
| Agent Premix Temperature | 70° F. (°C.) | | | | |
| Initial Fuel Temperature | 80° F. (°C.) | IPA | Acetone | IPA | Acetone |
| Foam Expansion Ratio | | 9.47 | 9.47 | 8.21 | 8.21 |
| Quarter Drain Time | min./sec. | 3:12 | 3:12 | 3:30 | 3:30 |
| 25% Coverage | min./sec. | 0:09 | 0:03 | 0:06 | 0:04 |
| 50% Coverage | min./sec. | 0:21 | 0:11 | 0:20 | 0:08 |
| 75% Coverage | min./sec. | 0:33 | 0:16 | 0:36 | 0:16 |
| 90% Control | min./sec. | 0:39 | 0:31 | 0:46 | 0:32 |
| 98% Control | min./sec. | 0:55 | 0:42 | 0:52 | 0:38 |
| Extinguishment | min./sec. | 1:00 | 0:51 | 0:57 | 0:47 |
| Fuel Exposed | min./sec. | 2:50 | 4:15 | 3:35 | 4:55 |
| 20% Burnback | min./sec. | 4:00 | 5:25 | 5:07 | 5:50 |

What is claimed is:

1. A water soluble foam stabilizer and film former comprising a polyamine with a molecular weight from 100 to 100,000 with 3 to 2200 nitrogens and a minimum of 3 primary or secondary amino groups, wherein said amino groups are partially or completely substituted by a) an oleophobic and hydrophobic perfluoroalkyl group, b) a hydrophilic group other than an amino group, and c) optionally a non-perfluoroalkyl hydrophobic group.

2. A water soluble foam stabilizer and film former according to claim 1, comprising a) segments of formula Ia and Ib

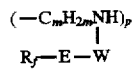 (Ia)

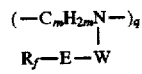 (Ib)

wherein $R_f$ is independently a straight or branched perfluoroalkyl group of 4 to 20 carbon atoms or said perfluoroalkyl substituted by perfluoroalkoxy of 2 to 6 carbon atoms, E is either zero or independently a divalent linking group and is a straight or a branched alkylene group of 1 to 16 carbon atoms or said alkylene group interrupted by one to three groups selected from the group consisting of —$NHR_1$—, —O—, —S—, —$SO_2$—, —COO—, —OOC—, —$CONR_1$—, —$NR_1CO$—, —$SO_2NR_1$—, —$NR_1SO_2$— or terminated at the $R_f$ end with —$CONR_1$— or —$SO_2NR_1$—, where $R_f$ is attached to the carbon or sulfur atom and wherein $R_1$ is independently hydrogen or alkyl of 1 to 6 carbon atoms, W is —CO— or —$SO_2$—, m is 2 to 10 and p and q are 0 to 500 and p+q are equal or larger than 1, b) segments of formula IIa and IIb and IIc,

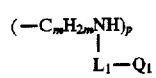 (IIa)

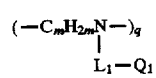 (IIb)

-continued

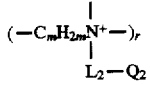 (IIc)

wherein $L_1$ is a divalent linking group and is a straight or branched saturated or unsaturated hydrocarbon group of 1 to 16 carbon atoms or said hydrocarbon group interrupted by one to three groups selected from —$NHR_1$—, —O—, —S—, —$CONR_1$—, —$NR_1CO$—, —$SO_2NR_1$—, —$NR_1SO_2$ or terminated with —CO— or —$SO_2$— where the linking group $L_1$ is attached to the nitrogen in formula IIa or IIb, $L_2$ is alkylene with 1 to 4 carbons, $Q_1$ is a hydrophilic group and is —COOH, —$SO_3H$ and salts thereof, —$CONH_2$, —$CONHCH_2OH$ or $(OCH_2CH_2)_nOH$;

$Q_2$ is —COO$^-$;

m is 2 to 10;

n is 1 to 10 and p and q are 1 to 500 and r is 0 to 500, c) optionally segments of formula IIIa and IIIb

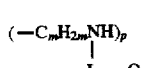 (IIIa)

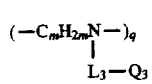 (IIIb)

wherein $L_3$ is zero, —CO— or —$SO_2$—, $Q_3$ is a straight or branched hydrocarbon group with 6 to 18 carbon atoms, m is 2 to 10 and p and q are 0 to 100.

3. A water soluble foam stabilizer and film former according to claim 1 comprising a) segments of formula Ia and Ib

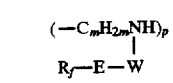 (Ia)

-continued

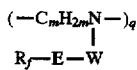

wherein $R_f$ is a straight or branched perfluoroalkyl group of 6 to 12 carbons, E is zero, —CH$_2$CH$_2$SCH$_2$—, —CH$_2$CH$_2$SCH$_2$CH$_2$—, —CH$_2$CH$_2$OCH$_2$CH$_2$—, W is —CO—, m is 2 and p and q are 0 to 100 and p+q are equal or larger than 1 b) segments of formula IIa, IIb and IIc

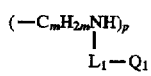

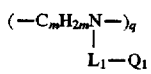

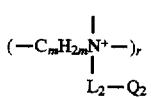

wherein

L$_1$ is —CH$_2$— and —CH$_2$CH$_2$—,

L$_2$ is —CH$_2$—,

Q$_1$ is —COOH and —COONa and

Q$_2$ is —COO$^-$, p and q are 1 to 100 and r is 0 to 100.

4. A water soluble foam stabilizer and film former according to claim 1, wherein the foam stabilizer and film former is derived from diethylenetriamine (DETA)

triethylenetetramine (TETA)

tetraethylenepentamine (TEPA)

pentaethylenehexamine (PEHA)

aminoethylpiperazine (AEP)

iminobispropylamine (IBPA).

5. A water soluble foam stabilizer and film former according to claim 1, wherein the foam stabilizer and film former is derived from polyethyleneimines with average molecular weights ranging from 300 to 70,000.

6. A method to improve the foam stability, polymeric film forming properties and fire fighting performance of polar solvent type aqueous film forming foam agents (AR-AFFF agents) based on fluorochemical surfactants, hydrocarbon surfactants, solvents, water and polysaccharide gums as polymeric film formers and optionally polymeric thickeners, fluorochemical synergists, electrolytes, pH buffers, corrosion inhibitors and the like by the addition of an effective amount of a foam stabilizer and film former comprising a polyamine with a molecular weight from 100 to 100,000 and 3 to 2200 nitrogens and a minimum of 3 primary or secondary amino groups wherein said aminogroups are partially or completely substituted by a) an oleophobic and hydrophobic perfluoroalkyl group, b) a hydrophilic group other than an amino group, and c) optionally a non-perfluoroalkyl hydrophobic group.

7. A method according to claim 6, wherein the water soluble foam stabilizer and film former comprises a) segments of formula Ia and Ib,

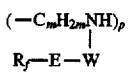

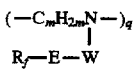

wherein $R_f$ is independently a straight or branched perfluoroalkyl group of 4 to 20 carbon atoms or said perfluoroalkyl substituted by perfluoroalkoxy of 2 to 6 carbon atoms, E is either zero of independently a divalent linking group and is a straight or a branched alkylene group of 1 to 16 carbon atoms or said alkylene group interrupted by one to three groups selected from the group consisting of —NHR$_1$—, —O—, —S—, —SO$_2$—, —COO—, —OOC—, —CONR$_1$—, —NR$_1$CO—, —SO$_2$NR$_1$—, —NR$_1$SO$_2$— or terminated at the R$_f$-end with —CONR$_1$— or —SO$_2$NR$_1$—, where R$_f$ is attached to the carbon or sulfur atom and wherein R$_1$ is independently hydrogen or alkyl of 1 to 6 carbon atoms, W is —CO— or —SO$_2$—, m is 2 to 10 and p and q are 0 to 500 and p+q are equal or larger than 1, b) segments of formula IIa and IIb and IIc,

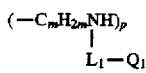

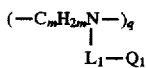

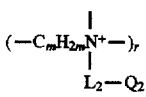

wherein

L$_1$ is a divalent linking group and is a straight or branched saturated or unsaturated hydrocarbon group of 1 to 16 carbon atoms or said hydrocarbon group interrupted by one to three groups selected from —NHR$_1$—, —O—, —S—, —CONR$_1$—, —NR$_1$CO—, —SO$_2$NR$_1$—, —NR$_1$SO$_2$ or terminated with —CO— or —SO$_2$— where the linking group L$_1$ is attached to the nitrogen in formula IIa or IIb;

L$_2$ is alkylene with 1 to 4 carbons,

Q$_1$ is a hydrophilic group and is —COOH, —SO$_3$H and salts thereof, —CONH$_2$, —CONHCH$_2$OH or (OCH$_2$CH$_2$)$_n$OH, Q$_2$ is —COO$^-$;

m is 2 to 10;

n is 1 to 10 and p and q are 1 to 500 r is 0 to 500, c) segments of formula IIIa and IIIb

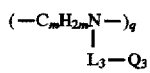

wherein

L$_3$ is zero, —CO— or —SO$_2$—, $Q_3$ is a straight or branched hydrocarbon group with 6 to 18 carbon atoms, m is 2 to 10 and p and q are 0 to 100.

8. A method according to claim 6, wherein the water soluble foam stabilizer and film former comprises a) segments of formula Ia and Ib

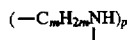
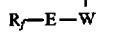

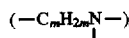
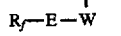

wherein $R_f$ is a straight or branched perfluoroalkyl group of 6 to 12 carbons, E is zero, —CH$_2$CH$_2$SCH$_2$—, —CH$_2$CH$_2$SCH$_2$CH$_2$—, —CH$_2$CH$_2$OCH$_2$CH$_2$—, W is —CO—, m is 2 and p and q are 0 to 100 and p+q are equal or larger than 1, b) segments of formula IIa, IIb and IIc

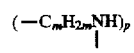

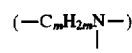

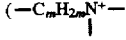

wherein $L_1$ is —CH$_2$—and —CH$_2$CH$_2$—, $L_2$ is —CH$_2$—, $Q_1$ is —COOH and —COONa and $Q_2$ is —COO$^-$, p and q are 1 to 100 and r is 0 to 100.

9. A method according to claim 6, wherein the water soluble foam stabilizer and film former is derive from diethylenetriamine (DETA)

triethylenetetramine (TETA)

tetraethylenepentamine (TEPA)

pentaethylenehexamine (PEHA)

aminoethylpiperazine (AEP)

iminobispropylamine (IBPA).

10. A method according to claim 6, wherein the foam stabilizer and film former is derived from polyethyleneimines with average molecular weights ranging from 300 to 70.000.

11. A method to convert aqueous film forming agents (AFFF agents) based on fluorochemical surfactants, hydrocarbon surfactants, solvents and water and optionally polymeric thickeners, fluorochemical synergists, electrolytes, pH buffers, corrosion inhibitors and the like useful to fight non-polar solvent and fuel fires into non-thixotropic polar solvent type aqueous film forming foam agents (AR-AFFF agents) capable of fighting both polar and non-polar solvent fires by the addition of an effective amount of a water soluble foam stabilizer and film former comprising a polyamine with a molecular weight from 100 to 100,000 with 3 to 2200 nitrogens and a minimum of 3 primary or secondary amino groups, wherein said aminogroups are partially or completely substituted by a) an oleophobic and hydrophobic perfluoroalkyl group, b) a hydrophilic group other than an amino group, and c) optionally a non-perfluoroalkyl hydrophobic group.

12. A method according to claim 11, wherein the water soluble foam stabilizer and film former comprises a) segments of formula Ia and Ib,

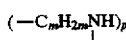
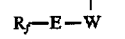

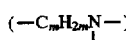
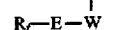

wherein $R_f$ is independently a straight or branched perfluoroalkyl group of 4 to 20 carbon atoms or said perfluoroalkyl substituted by perfluoroalkoxy of 2 to 6 carbon atoms, E is either zero of independently a divalent linking group and is a straight or a branched alkylene group of 1 to 16 carbon atoms or said alkylene group interrupted by one to three groups selected from the group consisting of —NHR$_1$—, —O—, —S—, —SO$_2$—, —COO—, —OOC—, —CONR$_1$—, —NR$_1$CO—, —SO$_2$NR$_1$—, —NR$_1$SO$_2$— or terminated at the R$_f$-end with —CONR$_1$— or —SO$_2$NR$_1$—, where R$_f$ is attached to the carbon or sulfur atom and wherein R$_1$ is independently hydrogen or alkyl of 1 to 6 carbon atoms, W is —CO— or —SO$_2$—, m is 2 to 10 and p and q are 0 to 500 and p+q are equal or larger than 1, b) segments of formula IIa and IIb and IIc,

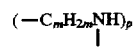

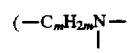

wherein $L_1$ is a divalent linking group and is a straight or branched saturated or unsaturated hydrocarbon group of 1 to 16 carbon atoms or said hydrocarbon group interrupted by one to three groups selected from —NHR$_1$—, —O—, —S—, —CONR$_1$—, —NR$_1$CO—, —SO$_2$NR$_1$—, —NR$_1$SO$_2$ or terminated with —CO— or —SO$_2$— where the linking group $L_1$ is attached to the nitrogen in formula IIa or IIb, $L_2$ is alkylene with 1 to 4 carbons, $Q_1$ is a hydrophilic group and is —COOH, —SO$_3$H and salts thereof, —CONH$_2$, —CONHCH$_2$OH or (OCH$_2$CH$_2$)$_n$OH, $Q_2$ is —COO$^-$;

m is 2 to 10;

n is 1 to 10 and p and q are 1 to 500 and r is 0 to 500.

c) optionally segments of formula IIIa and IIIb

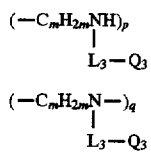  (IIIa)

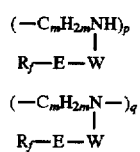  (IIIb)

wherein $L_3$ is zero, —CO— or —SO$_2$—, $Q_3$ is a straight or branched hydrocarbon group with 6 to 18 carbon atoms, m is 2 to 10 and p and q are 0 to 100.

13. A method according to claim 11 wherein the water soluble foam stabilizer and film former comprises a) segments of formula Ia and Ib $$(-C_mH_{2m}NH)_p \quad (Ia)$$
$$\hspace{1em}|$$
$$R_f-E-W$$

$$(-C_mH_{2m}N-)_q \quad (Ib)$$
$$\hspace{1em}|$$
$$R_f-E-W$$

wherein $R_f$ is a straight or branched perfluoroalkyl group of 6 to 12 carbons, E is zero, —CH$_2$CH$_2$SCH$_2$—, —CH$_2$CH$_2$SCH$_2$CH$_2$—, —CH$_2$CH$_2$OCH$_2$CH$_2$—, W is —CO—, m is 2 and p and q are 0 to 100 and p+q are equal or larger than 1.

b) segments of formula IIa, IIb and IIc

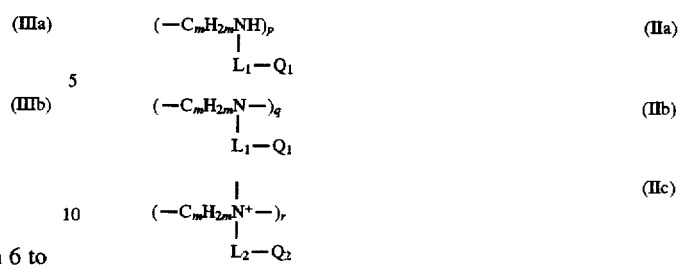

wherein $L_1$ is —CH$_2$—and —CH$_2$CH$_2$—, $L_2$ is —CH$_2$—, $Q_1$ is —COOH and —COONa, $Q_2$ is —COO$^-$, p and q are 0 to 100 and r is 0 to 100.

14. A method according to claim 11, wherein the water soluble foam stabilizer and film former is derived from
diethylenetriamine (DETA)
triethylenetetramine (TETA)
tetraethylenepentamine (TEPA)
pentaethylenehexamine (PEHA)
aminoethylpiperazine (AEP)
iminobispropylamine (IBPA).

15. A method according to claim 11, wherein the foam stabilizer and film former is derived from polyethyleneimines with average molecular weights ranging from 300 to 70,000.

* * * * *